US008045775B2

(12) United States Patent
Volkau et al.

(10) Patent No.: US 8,045,775 B2
(45) Date of Patent: Oct. 25, 2011

(54) LOCALIZATION OF BRAIN LANDMARKS SUCH AS THE ANTERIOR AND POSTERIOR COMMISSURES BASED ON GEOMETRICAL FITTING

(75) Inventors: Ihar Volkau, Singapore (SG); Bhanu K N Prakash, Singapore (SG); Ting Ting Ng, Singapore (SG); Varsha Gupta, Matrix (SG); Wieslaw L. Nowinski, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 466 days.

(21) Appl. No.: 12/438,080

(22) PCT Filed: Aug. 24, 2007

(86) PCT No.: PCT/SG2007/000274
§ 371 (c)(1),
(2), (4) Date: Feb. 19, 2009

(87) PCT Pub. No.: WO2008/024082
PCT Pub. Date: Feb. 28, 2008

(65) Prior Publication Data
US 2010/0172553 A1  Jul. 8, 2010

Related U.S. Application Data

(60) Provisional application No. 60/839,711, filed on Aug. 24, 2006.

(51) Int. Cl.
*G06K 9/00* (2006.01)

(52) U.S. Cl. ........................................ 382/128; 382/131
(58) Field of Classification Search ........... 382/128–134
See application file for complete search history.

(56) References Cited

U.S. PATENT DOCUMENTS 5,119,816 A * 6/1992 Gevins .......................... 600/383
7,239,910 B2 * 7/2007 Tanner .......................... 600/544

FOREIGN PATENT DOCUMENTS

WO  WO 2005/048844 A1  6/2005
WO  WO 2006/011850 A1  2/2006

OTHER PUBLICATIONS

Prakash, K.N. et al., "Morphologic Relationship Among the Corpus Callosum, Fornix, Anterior Commissure, and Posterior Commissure", Academic Radiology, Reston, VA, vol. 13, No. 1, Jan. 1, 2006, pp. 24-35.

(Continued)

*Primary Examiner* — David Mis
(74) *Attorney, Agent, or Firm* — Baker & Daniels LLP

(57) ABSTRACT

A method of estimating the location of the anterior and posterior commissures in a brain scan image is proposed. Firstly, a geometrical object is constructed using points on a brain scan image of an individual which are on the surface of the brain, such as an ellipse fitting the cerebral surface of a sagittal image of the mid-sagittal plane, or an adjacent sagittal plane. The locations on the MSP of the AC and PC landmarks (and optionally other landmarks) are estimated using the five parameters which define the ellipse, plus numerical values obtained in advance from statistical analysis of other individuals.

11 Claims, 2 Drawing Sheets

OTHER PUBLICATIONS

Bhanu Prakash, K.N. et al., "Rapid and Automatic Localization of the Anterior and Posterior Commissure Point Landmarks in MR Volumetric Neuroimages", Academic Radiology, Reston, VA, vol. 13, No. 1, Jan. 1, 2006, pp. 36-54.

Hu, Q. et al., "Knowledge-Driven Extraction of the Four Modified Talairach Cortical Landmarks (A, P, L, and R) from MR Neuroimages", Bioinformatics and Bioengineering, 2004, BIBE 2004, Fourth IEEE Symposium on Taichung, Taiwan, ROC May 19-21, 2004, Piscataway, NJ, IEEE, May 19, 2004, pp. 93-99.

Yu, H.S. et al., "Anatomic Labelling of PET Brain Images with Automatic Detection of AC and PC", Journal of Digital Imaging; The Journal of the Society for Computer Applications in Radiology, Springer-Verlag, NE, vol. 11, No. 3 Supp. 1, Aug. 1, 1998, pp. 56-58.

Han, Y. et al., "Automatic Registration of Brain Magnetic Resonance Images Based on Talairach Reference", Journal of Magnetic Resonance Imaging, Society for Magnetic Resonance Imaging, Oak Brook, IL, vol. 20, No. 4, Oct. 1, 2004, pp. 572-580.

Verard, L. et al., "Fully Automatic Identification of AC and PC Landmarks on Brain MRI Using Scene Analysis", IEEE Transactions on Medical Imaging, IEEE Service Center, Piscataway, NJ, vol. 16, No. 5, Oct. 1, 1997, pp. 610-616.

Search Report and Written Opinion for PCT/SG2007/000274 issued by the European Patent Office on Jul. 25, 2008.

International Preliminary Report on Patentability from PCT/SG2007/000274.

* cited by examiner (a)          (b)

LOCALIZATION OF BRAIN LANDMARKS SUCH AS THE ANTERIOR AND POSTERIOR COMMISSURES BASED ON GEOMETRICAL FITTING

CROSS-REFERENCE TO RELATED APPLICATIONS

This application is a U.S. National Phase Application of PCT International Application No. PCT/SG2007/000274, filed on Aug. 24, 2007, which claims the benefit of U.S. Application Ser. No. 60/839,711, filed on Aug. 24, 2006, both of which are expressly incorporated by reference herein.

FIELD OF THE INVENTION

The present invention relates to methods for locating landmarks, particularly the anterior and posterior commissures, on neuroimages (i.e. brain scan images). It further relates to systems arranged to perform these methods.

BACKGROUND OF THE INVENTION

The human body demonstrates definite proportions. The same is true for proportions of the head. The systematic study of brain proportions and morphometry could start only with the development of in vivo techniques of brain visualisation. Attempts to establish the relationship between landmarks on the skull and anatomical structures within the brain were undertaken starting from the beginning of $19^{th}$ century. Use of this technique in patients was not practical because of variability in the spatial relationship between sub-cortical structures and cranial landmarks until intracerebral reference points could be located and correlated to sub-cortical target structures. Using a system of coordinates defined based on the brain can help in location of sub-cortical structures. The Talairach and Tournoux (TT) system of coordinates is based on 6 external landmarks and 2 internal landmarks (the anterior commissure—AC and posterior commissure—PC).

The human cerebrum comprises of two hemispheres that exchange information with each other through axons, which are arranged in specific bundles called commissures. The anterior commissure (AC) and posterior commissure (PC) are two such structures. Identification of AC and PC is critical not only because they are important brain structures, but also because their location is crucial in stereotactic and functional neurosurgery [1], localization analysis in human brain mapping [2], medical image analysis [3], structure segmentation and labeling in neuroradiology [4] as well as in registration to reduce the number of degrees of freedom. Major stereotactic brain atlases, such as the Talairach and Tournoux (TT) brain atlas [5], the Referentially Oriented Talairach-Tournoux atlas [6] and the Schaltenbrand-Wahren atlas [7] are based on the AC and PC. The Talairach transformation based on AC and PC is also widely used in human brain mapping for brain comparison across subjects [8]. In addition, the number of references to the TT atlas has been growing exponentially [9].

The AC and PC structures are often hard to detect due to their small size, variability in intensity properties, low data resolution in comparison to their size, presence of neighboring structures with similar appearance (e.g., the fornix, blood vessels) and noise. For neuroanatomy experts, an interactive identification of AC and PC is straightforward for high quality data. However, automation is desirable not only in research but also in clinical practice to increase confidence with which these structures can be identified by a non-neuroradiologist or other non-specialist (e.g., in urgent cases), and to save a substantial amount of time when processing numerous datasets. Extraction of the AC and PC landmarks from T1WI neuroimages is described in [10, 11]. Some spatial properties of cerebral structures and the anterior and posterior commissures were presented in [12, 13]. In paper [12] quantitative and statistical analysis of angles and distances related to the inter-commissural line has been done. In particular the mean length of the inter-commissural line and range were found for 50 subjects. However, none of these results were correlated to the shape of the brain.

In the case that only low-resolution images of the brain are available, a large interslice gap and partial effects might cause partial visibility or non-visibility of the AC and PC landmarks. Non-morphological cerebral images, such as perfusion-weighted images (PWI) (e.g. a CBF map which indicates cerebral blood flow) and diffusion-weighted images (DWI), do not reflect anatomy and this makes it impossible to detect anatomical structures directly. FIG. 1(a) is an example of a CBF image and FIG. 1(b) is an example of a DWI image.

SUMMARY OF THE INVENTION

The present invention aims to provide a new and useful method to derive the anterior and posterior commissures (AC and PC) from the shape of a brain surface, and in particular a method which is suitable to derive the AC and PC landmarks from low-resolution and non-morphological cerebral images.

In general terms the invention proposes that a geometrical object is constructed using points on a brain scan image of an individual which are on the surface of the brain, and that numerical values, obtained by a prior statistical analysis of images of other individuals, are used to estimate the locations of the anterior and posterior commissures by reference to the geometrical object.

Preferably the image is a sagittal image including the MSP, or more preferably a sagittal image which is the maximum intensity projection (MIP) of a sagittal is slab including the MSP. A number of points on the cerebral surface of the sagittal image are selected, and an ellipse is constructed to fit the points. The locations on the sagittal image of the AC and PC landmarks (and optionally other landmarks) are estimated using the five parameters which define the ellipse, plus numerical values obtained in advance from statistical analysis of other individuals.

The present method is found to provide acceptable accuracy and be applicable, even for neuroimages of low quality, in obtaining the AC and PC landmarks provided that the cortex is visible in the neuroimage. The method is applicable for isotropic as well as anisotropic volumes (in the latter case the coordinates are mapped into isotropic space).

Embodiments of the invention can be used in multiple applications, for example:

For registration of diffusion-perfusion images, e.g. for stroke processing.

Atlas-data mapping for incomplete acquisition, i.e. when the patient neuroimage does not contain the complete brain scan (e.g. if the scan contains only the subcortical, frontal and occipital regions, the ellipse constructed by an embodiment of the invention may still be approximately the same).

For intra-patient registration. If several studies of the same patient are performed using different modalities (e.g. T1, T2, FLAIR, and DWI pulse sequences) the ellipse equations are approximately the same, and this reduces the number of degrees of freedom for the registration.

For localization of the region of interest (ROI) for structures. That is, using the technique it is possible to identify regions in which more detailed examination should be carried out, i.e. successive segmentation.

BRIEF DESCRIPTION OF THE DRAWINGS

An embodiment of the invention will now be described, for the sake of example only, with reference to the following drawings, in which.

DETAILED DESCRIPTION OF THE EMBODIMENT

Figure 1:
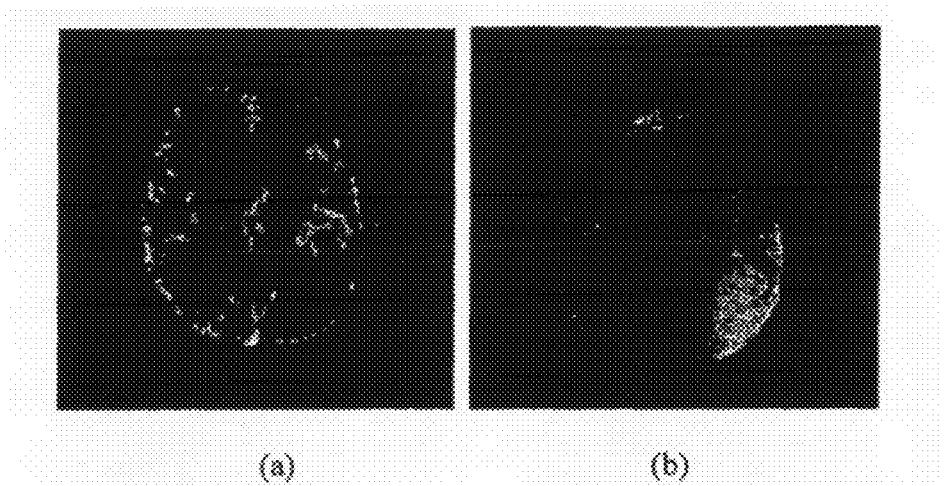
FIG. 1 is composed of FIGS. 1(a) and 1(b) which respectively show a CBF map of PWI and a DWI image of axial slices a brain.
Figure 2:
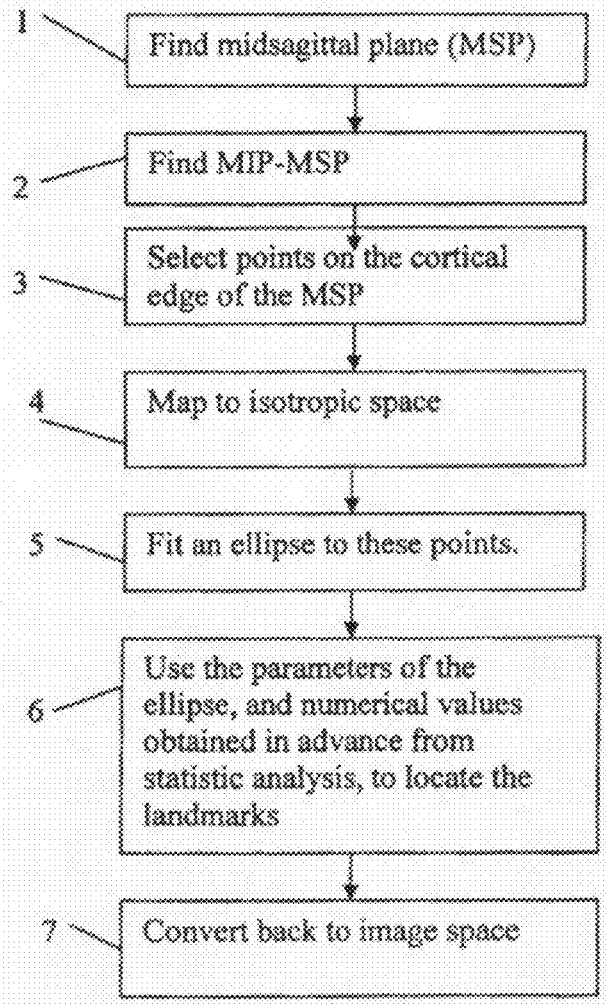
FIG. 2 is a flow diagram of the steps of the method.
Figure 3:
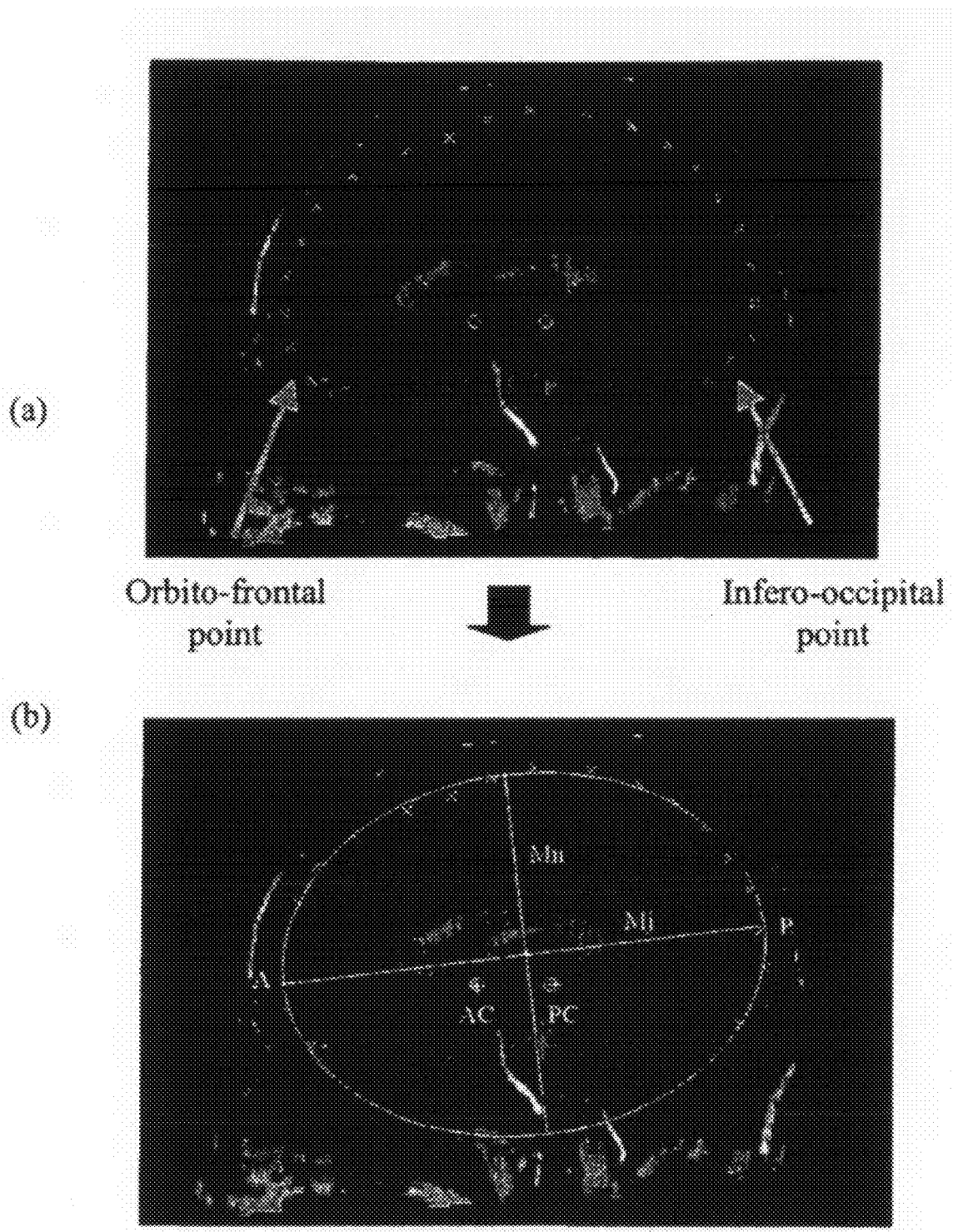
FIG. 3, which is composed of FIGS. 3(a) and 3(b), illustrates schematically the operation of the embodiment.

A method which is an embodiment of the invention will now be described with reference to FIGS. 2 and 3. Processing of neuroimage comprises of the following major steps shown in FIG. 2 (the volume is assumed to be in radiological convention).

1. Find the midsagittal plane (MSP) of the cerebral volume (e.g. by using the algorithm from [14]).
2. Set a slab of say ±2 mm about the MSP to construct a new slice using the maximum intensity projection (MIP) of the sagittal slices in this range. Let this slice be referred as MIP-MSP.
3. Select points on the cortical edge on the MIP-MSP between the orbito-frontal and infero-occipital point landmarks of the brain (FIG. 3a). A recommended number of points to choose should be 15 or more to ensure the robustness of the fit. These points should preferably be evenly-distributed and should cover the entire region in between the orbito-frontal cortex and occipital cortex of the brain, especially at points where the curvature is large.
4. The points obtained in the previous step are mapped into an isotropic space, without reformatting the data before fitting the ellipse. This is done to have the points in a uniform coordinate system.
5. Fit the ellipse [15] to the points marked at the MSP plane at previous step. Find parameters (the major and minor axes, center point, and inclination) of the ellipse. The ellipse axes define a system of coordinates, connected with the MSP cut of the brain.

Let (see FIG. 3(b))

A denote the point of intersection of the ellipse and the major axis at the anterior part of the head;
P denote the point of intersection of the ellipse and the major axis at the posterior part of the head;
$D_{AC}$ ($D_{PC}$) denote the distance (in mm) between point A and commissure AC (PC).
$\phi_{AC}$ ($\phi_{PC}$) denote the angle (in degrees) defined by points P, A and commissure AC (PC).
U denote the unit vector, collinear to the direction of major axis (vector AP);
Mj and Mn denote the lengths of semi-major and minor axes of the ellipse;
Θ denote the angle (in degrees) between the major axis and acquisition (axial) plane.

6. Locate the position of the AC and PC points by using the parameters of the ellipse.

The anterior commissure can be found as the endpoint of vector $d_{Ac}*U$ rotated clockwise by an angle $\alpha_{Ac}$ around the pivot point A. The posterior commissure is defined by using vector $d_{pc}*U$ and angle $\alpha_{pc}$; $d_{AC}$, $d_{PC}$, $\alpha_{AC}$ to and $\alpha_{PC}$ are the constant of proportionality.

The method proposed calculates distances (in mm) between point A and commissure AC (PC) as $d_{AC}*Mj$ and $d_{PC}*Mj$ respectively;

angles (in degrees) defined by points P, A and commissure AC (PC) as $\alpha_{Ac}*Mj$ and $\alpha_{PC}*Mj/Mn$ respectively.

The numerical values of the constants for localization are obtained in advance from statistical analysis given in the following table.

TABLE 1

Regression statistics: parameters of proportionality, goodness of fit $R^2$ and 95% confidence intervals for the slopes corresponding to linear fit between parameters.

| Constants of proportionality | Correlation | Slope | Adjusted $R^2$ | Lower 95% | Upper 95% |
| --- | --- | --- | --- | --- | --- |
| $\alpha_{AC}$ | ($\Phi_{AC}$, Mj) | 0.0967 | 0.92 | 0.0893 | 0.1040 |
| $d_{AC}$ | ($D_{AC}$, Mj) | 0.7873 | 0.98 | 0.7800 | 0.7945 |
| $\alpha_{PC}$ | ($\Phi_{PC}$, Mj/Mn) | 5.464 | 0.90 | 4.9906 | 5.9374 |
| $d_{PC}$ | ($D_{PC}$, Mj) | 1.1143 | 0.98 | 1.1061 | 1.1225 |

The numerical values mentioned here apply to isotropic volumes only. They are obtained based on a statistical analysis. For the training set the mean and standard deviation of the absolute value (in mm) of the Euclidean error of localization using these equations are [2.35, 1.37] for the AC and [3.12, 1.75] for the PC. The mean and standard deviation for the test set are [1.76, 0.67] and [2.67, 1.16] for AC and PC, respectively.

7. Convert back the coordinates of AC and PC into the acquired image space.

Note that in variations of the embodiment, any other point on the ellipse, inside or outside it, not only A, can be used. In this case, the numerical parameters would be different, but could be obtained by a procedure similar to the following one.

Note further that if the original image has low resolution or artifacts (i.e. diffusion weighted image with the susceptibility artifacts or perfusion weighted image) it may cause the ellipse on the MIP-MSP found in step 5 be either underestimated or overestimated. The process of calculating the ellipse in this case is different. For each axial slice we segment the brain area and obtain its edge; an ellipse is fitted [15] to the edge in axial direction; its anterior and posterior points are obtained and these points are projected to the MSP.

To analyze the statistical properties of the commissure localization process in accordance with slopes obtained in Table 1 we examined the following sets of parameters for the training dataset:

1. Angle $\phi_{AC}$ between major axis and vector going from A to anatomical AC (degrees), divided by Mj.
2. Distance $D_{AC}$ from A to anatomical AC divided by Mj.
3. Angle (degrees) between vectors going from A to anatomical AC and from A to calculated AC.
4. The deviation between anatomical and calculated AC points (projection to A-AC line, mm) denoted as AC_X.
5. The deviation between anatomical and calculated AC points (projection to line orthogonal to A-AC line, mm) denoted as AC_Y.
6. Angle $\phi_{PC}$ between major axis and vector going from A to anatomical PC (degrees), divided by (Mj/Mn).
7. Distance $D_{PC}$ from A to anatomical PC divided by Mj.
8. Angle (in degrees) between vectors going from A to anatomical PC and from A to calculated PC.
9. The deviation between anatomical and calculated PC points (projection to A-PC line, mm) denoted as PC_X.
10. The deviation between anatomical and calculated PC points (projection to line orthogonal to A-PC line, mm) denoted as PC_Y.

Statistical parameters and results of the null hypothesis check (the data are normally distributed) are summarized in the Table 2.

TABLE 2

Results of Test of Normality of training datasets

| Set of parameters | KS Lilliefors 2-tail test statistics (p-value) | Shapiro-Wilk test statistics (p-value) | Mean | Std |
|---|---|---|---|---|
| #1 | 0.10 (0.29) | 0.98 (0.50) | 0.0963 | 0.02 |
| #2 | 0.11 (0.24) | 0.98 (0.67) | 0.7873 | 0.02 |
| #3 | 0.09 (0.53) | 0.98 (0.53) | 0.02 | 1.84 |
| #4 | 0.10 (0.30) | 0.98 (0.63) | −0.04 | 1.81 |
| #5 | 0.08 (0.71) | 0.98 (0.58) | 0.00 | 2.01 |
| #6 | 0.10 (0.30) | 0.96 (0.10) | 5.6253 | 1.52 |
| #7 | 0.10 (0.27) | 0.98 (0.61) | 1.1146 | 0.03 |
| #8 | 0.10 (0.28) | 0.97 (0.33) | −0.10 | 1.91 |
| #9 | 0.11 (0.21) | 0.98 (0.52) | −0.03 | 2.06 |
| #10 | 0.11 (0.18) | 0.98 (0.48) | 0.10 | 2.91 |

The Pearson correlation coefficient between AC_X and AC_Y errors is 0.177 (probability of chance fluctuation=0.19) and between PC1 X and PC1 Y errors is −0.096 (probability of chance fluctuation=0.48). Mardia's multivariate normality test [18, 19] shows that the data sets (AC_X, AC_Y) and (PC_X, PC_Y) are similar to the normal bivariate distributions.

The results of the Shapiro-Wilk test and the K-S Lilliefors test show (Table 2) that we cannot reject the null hypothesis that sets of parameters #1, #2, #6, #7 are normally distributed as the p-values for all the cases are greater than 0.05. It means we can use the mean values of these distributions for parameters' estimation. The mean values and the values received by the LSE method are close to each other (see Table 1: mean value for each distribution is inside 95% confidence interval for the parameter calculated using LSE method).

In statistical model-fitting, an indicator of goodness of fit is that the residuals (the errors) should be independent and normally distributed with the mean value close to zero. To find the normality of the residuals (for sets of parameters #3-5 and #8-10) we conducted Shapiro-Wilk and K-S Lilliefors test with α=0.05. The results are tabulated in Table 2. Since the corresponding p-values are greater than 0.05, it can be inferred that all the residuals are normally distributed. In the special case when two randomly distributed variables are jointly normal, independence is equivalent to uncorrelatedness.

The Pearson correlation coefficient between AC_X and AC_Y errors is 0.177 (probability of chance fluctuation=0.19) and between PC_X and PC_Y errors is −0.096 (probability of chance fluctuation=0.48). As the probability of chance fluctuation is much larger than 0.05, these correlations are insignificant and we can conclude that little or no association between these errors exists (i.e. low errors in X direction are associated with both low and high errors in Y direction; high errors in Y direction are also associated with both low and high errors in X direction). By virtue of Mardia's test result a random vector (AC_X, AC_Y) (as well as (PC_X, PC_Y)) has a multivariate normal distribution, so two its uncorrelated components are independent and normally distributed, and this can be considered as an indicator of goodness of fit.

In order to check the robustness of the values of parameters obtained by the procedure described in earlier sections, we performed the following simple test. The errors in AC and PC position were obtained by comparing their values with the AC and PC position determined manually (using anatomy). The errors in AC and PC position are carried forward in estimating other parameters like AC-PC distance and angle between AC (or PC) position and major semi axis of the ellipse.

During these experiments, the following additional observations were made:

1. The center of ellipse lay on the massa intermedia structure, if this structure is visible on the MSP (according to [17] it is missing in about 20% of human brains).
2. Applications of the ellipse fitting procedure and the system of coordinates, defined by this ellipse, gave us a way to perform an intra-patient registration for both morphological as well as non-morphological images, which will be useful for stroke image processing. This mapping can be considered as an initial approximation for a subsequent fine tuning stage of registration.
3. The results of the ellipse fitting algorithm are robust even when data are subsampled and incomplete.
4. The applications of the approach proposed can be extended for localization of other points and distributed landmarks. For example, with the positions of AC and PC located, subcortical structures like the corpus callosum and the fornix which are at a distance to the commissures can be located based on statistical analysis as described in [13]. Statistical localization of other points and landmarks in the system of coordinates obtained can be used for defining an ROI for these structures during segmentation as well as for intra-patient registration (especially in registration of morphological and non-morphological (diffusion and perfusion weighted) images for stroke image processing) and registration against atlas.
5. Statistical localization described could be useful for low resolution data when localization error is comparable with image resolution. The position of the landmark calculated might be between the slices of the image under processing.

Obviously, a probabilistic method cannot provide the accuracy of the direct extraction of landmarks from the image. However if the landmarks are not visible, the probabilistic approach can be useful. The technique may be applied when analyzing different types of scans in patients with strokes in a short amount of time. In this case the clinical scans are of low resolution and have large slice thickness and, consequently the identification of brain landmarks is extremely difficult. Therefore, for the identification of strokes this method could be sufficient when location of structures is done with acceptable accuracy. In cases when high resolutions scans are available, e.g. stereotaxic and functional neurosurgery as well as human brain mapping experiments, there will typically be no need to use this method.

REFERENCES

1. Nowinski W L. (2001): Modified Talairach landmarks. Acta Neurochirugica 43(10):1045-1057.
2. Nowinski W L, Thirunavuukarasuu A. 2003. A locus driven mechanism for rapid and automated atlas assisted analysis of functional images by using the Brain Atlas for Functional Imaging.
3. Lacerda A L T, Hardan A Y, Yorbik O, Keshavan M S. (2003): Measurement of the orbitofrontal cortex: a validation study of a new method. Neuroimage 19: 665-673
4. Nowinski W L. 2002. Electronic brain atlases: features and applications in 3D Image processing: Springer-Verlag. 79-93.
5. Talairach J, Tournoux P. 1988. Coplanar Stereotactic Atlas of the Human Brain: George Thieme/Verlag/Thieme Medical Publishers, Stuttgart-New York.

6. Talairach J, Toumoux P. 1993. Referentially oriented cerebral MRI anatomy: George Thieme/Verlag/Thieme Medical Publishers, Stuttgart-New York.
7. Schaltenbrand G, Wahren W. 1977. Guide to the Atlas for Stereotaxy of the Human Brain: Georg Thieme Publishers. Stuttgart.
8. Lancaster J L, FOX P T. 2000. Talairach space as a tool for intersubject standarization in the brain. San Diego: Academic Press. 555-567.
9. Fox P T, Parson L M, Lancaster J L. (1998): Beyond the single study: functional/location metanalysis in cognitive neuroimaging. Current Opinions in Neurobiology 8:178-187.
10. Bhanu Prakash K N, Hu Q, Aziz A, Nowinski W L: Rapid and automatic localization of the anterior and posterior commissure point landmarks in MR volumetric neuroimages. Academic Radiology, 13(1) 2006:36-54.
11. Bhanu Prakash K N, Nowinski W L, Automatic detection of anterior and posterior commissure landmarks, BIL/P// 1390/SG; SG 200306861-6, filed 19 Nov. 2003. WO 2005/048844 A1, 2 Jun. 2005.
12. Steven Bauserman, Russell Meyers, William J. Fry. Spatial variations between certain cranial and cerebral structures and the anterior and posterior commissures of the living human. The Anatomical Record, Volume 146, Issue 1, 1963, pp. 1-6.
13. Bhanu Prakash K N, Nowinski W L, Morphological relationship among the corpus callosum, fornix, anterior commissure and posterior commissure: MRI-based variability study. Academic Radiology, 13(1) 2006: 24-35.
14. Bhanu Prakash K N, Volkau I, Nowinski W L, Locating a mid-sagittal plane, BIL/P//1666/US filed on 2 Apr. 2004. BIL/P/1666/2475/PCT. PCT/SG2005/000106 application filed on 1 Apr. 2005. WO 2005/096227 A1 published on 13 Oct. 2005. (former invention title: *Extraction of mid-sagittal plane from MR brain volume-Entropy and energy based approaches*)
15. Fitzgibbon A., Pilu M., Fisher R.: Direct least-square fitting of Ellipses, IEEE Transactions on Pattern Analysis and Machine Intelligence, 21 (1999) 476-480
16. P. R. Bevington, Data Reduction and Error Analysis for the Physical Sciences. McGraw-Hill, New York; 1969.
17. Allen L S, Gorski R A. Sexual dimorphism of the anterior commissure and massa intermedia of the human brain. J Comp Neurol. 1991 Oct. 1; 312(1):97-104.
18. Mardia K V, 1970. Measures of multivariate skewnees and kurtosis with applications. Biometrika, 57(3):519-530.
19. Mardia K V, 1974. Applications of some measures of multivariate skewness and kurtosis for testing normality and robustness studies. Sankhya A, 36:115-128.

The invention claimed is:

1. A method of estimating the position of one or more landmarks, including at least one of the AC and PC landmarks, within an image of the brain of an individual, the method including:
   (a) identifying on the image a plurality of points on the surface of the brain;
   (b) using the identified points to construct a geometrical object in the space of the image and defined by a plurality of parameter values; and
   (c) using the geometrical object, and one or more numerical values derived in advance statistically from other individuals, to estimate the position of the one or more landmarks.

2. A method according to claim 1 in which the image includes a sagittal plane of the brain, the plurality of points are points on the cortical edge on the sagittal plane, and the geometrical object is an ellipse, step (b) of constructing the ellipse being performed by fitting the ellipse to the points.

3. A method according to claim 2 in which the sagittal plane is at or proximate the mid-sagittal plane of the brain.

4. A method according to claim 1, in which there are a plurality of said numerical values, and the position of at least one of the landmarks is obtained using at least two of the numerical values.

5. A method according to claim 4 in which the position of one of the landmarks is estimated by:
   (i) multiplying a dimension of the geometrical object by a first of said numerical values to obtain a distance measure;
   (ii) choosing a location in the image using the geometrical object; and
   (iii) estimating the location of the landmark to be at a distance from the chosen location defined by the distance measure, and at an orientation relative to the chosen location defined by a second of the numerical values.

6. A method according to claim 2 in which the position of one of the landmarks is estimated by:
   (i) multiplying the length of the major axis of the ellipse by a first of said numerical values to obtain a distance measure;
   (ii) choosing a location in the image using the ellipse; and
   (iii) estimating the location of the landmark to be at a distance from the chosen location defined by the distance measure, and at an orientation relative to the chosen location defined by a second of the numerical values.

7. A method of registering at least two brain scan images, the method including obtaining for each of the at least two images an estimate of the positions of a plurality of landmarks within each image by a method according to claim 1, and using the corresponding estimated positions to register the images.

8. A method of identifying a region of interest on an image, the method comprising obtaining an estimate of the positions of at least one landmarks within the image by a method according to claim 1, and identifying the region of interest in relation to the at least one of the landmark.

9. A method according to claim 1 comprising a preliminary step of determining whether the image is isotropic, and if not converting the image into an isotropic image, said geometrical object defined in the space of the isotropic image.

10. A system for estimating the position of one or more landmarks, including at least one of the AC and PC landmarks, within an image of the brain of an individual, the system including a processor arranged to:
    (a) receive the image of the brain of the individual;
    (b) register a plurality of points on the image which are on the surface of the brain;
    (c) use the identified points to construct a geometrical object in the space of the image and defined by a plurality of parameter values; and
    (d) using the geometrical object, and one or more predefined numerical values representative of typical individuals, to estimate the position of the one or more landmarks.

11. A computer program product comprising software which, upon being run by a computer system, causes the computer system to estimate the position of one or more landmarks, including at least one of the AC and PC landmarks, within an image of the brain of an individual, by:
(a) registering the choice of a plurality of points in the image which are on the surface of the brain;
(b) using the identified points to construct a geometrical object in the space of the image and defined by a plurality of parameter values; and
(c) using the geometrical object, and one or more predefined numerical values representative of typical individuals, to estimate the position of the one or more landmarks.

* * * * *